United States Patent [19]

Paskar

[11] Patent Number: 5,290,229
[45] Date of Patent: Mar. 1, 1994

[54] TRANSFORMABLE CATHETER AND METHOD

[76] Inventor: Larry D. Paskar, 14337 Stablestone Ct., Chesterfield, Mo. 63017

[21] Appl. No.: 730,120

[22] Filed: Jul. 15, 1991

[51] Int. Cl.[5] ............................................. A61M 37/00
[52] U.S. Cl. .................................... 604/95; 604/281; 604/283; 128/657
[58] Field of Search .......... 604/95, 264, 171, 280–283, 604/158, 164; 128/656–658, 772

[56] References Cited

U.S. PATENT DOCUMENTS

| | | | |
|---|---|---|---|
| 3,503,385 | 3/1970 | Stevens . | |
| 4,353,358 | 10/1982 | Emerson | 128/4 |
| 4,405,314 | 9/1983 | Cope | 604/281 |
| 4,430,083 | 2/1984 | Ganz et al. | 604/283 |
| 4,512,765 | 4/1985 | Muto | 604/281 |
| 4,581,017 | 4/1986 | Sahota | 604/101 |
| 4,586,923 | 5/1986 | Gould et al. | 604/95 |
| 4,694,838 | 9/1987 | Wijayarthna et al. | 604/281 |
| 4,898,577 | 2/1990 | Badger et al. | 604/282 |
| 4,911,148 | 3/1990 | Sosnowski et al. | 128/4 |
| 4,925,445 | 5/1990 | Sakamoto et al. | 128/772 |
| 4,935,017 | 6/1990 | Sylvanowicz | 604/280 |
| 5,016,640 | 3/1991 | Ruiz | 604/281 |

FOREIGN PATENT DOCUMENTS 2923633 12/1980 Fed. Rep. of Germany .

Primary Examiner—C. Fred Rosenbaum
Assistant Examiner—Mark Bockelman
Attorney, Agent, or Firm—Polster, Lieder, Woodruff & Lucchesi

[57] ABSTRACT

A transformable catheter includes a sheath having a length which is a substantial fraction of the entire length of the transformable catheter and a bore therethrough. A preformed inner catheter having a complex curve formed into the distal end thereof is disposed in the sheath bore. By axially moving the inner catheter with respect to the sheath, various tip shapes may be achieved. At least one wire runs from the proximal end of the sheath to the vicinity of the distal end of the sheath to selectively deflect the distal tip of the sheath as desired by the user to assist in reformation and transformation of the tip of the catheter. By suitable manipulation of the wire and of the inner catheter with respect to the sheath, the shape of the exposed portion of the distal end of the inner catheter may be transformed to any of a variety of shapes.

23 Claims, 2 Drawing Sheets ium. The sheath has

TRANSFORMABLE CATHETER AND METHOD

CROSS REFERENCE TO DISCLOSURE DOCUMENT

This application concerns the invention disclosed to the Patent Office in Disclosure Document 282,214, filed May 20, 1991.

BACKGROUND OF THE INVENTION

This invention relates generally to medical devices, and more particularly to a catheter which can be formed, inside the human body, into a vast number of different shapes.

Selective catheterization of cerebral and visceral branch arteries is often difficult and at times impossible in some patients—particularly older patients with very tortuous and ectatic vasculature. Successful catheterization sometimes requires multiple catheter exchanges for various shaped catheters. It is not uncommon to easily catheterize three of four vessels for a four vessel head study, only to find that the fourth vessel (generally the left or right carotid) requires an entirely different catheter shape and tip orientation. It would be desirable if one could easily and simply reshape the catheter and reorient the tip to direct it into the vessel orifice, instead of depending on several complex catheters that require reformation, fancy torque and advancing maneuvers, body english and, above all, luck.

Tip reorientation, the goal of most prior devices which have addressed the problem, is only half of what is needed to make a truly workable universal catheter. Numerous catheter curve configurations have been conceived not only to reorient the tip properly for selection of branch vessels, but also to provide anchorage of the catheter against the aortic wall. A wide looped long tipped sidewinder III configuration with an exaggerated retrocurve is one such example of a highly specialized complex catheter.

This anchorage or wedge effect against the aortic wall lessens the recoil caused by the "jet effect" during high pressure contrast injection which might otherwise cause the catheter to flip out of the selected branch vessel (particularly in short branch vessels or at levels of a dilated aorta).

These complex configurations, therefore, evolved not only to orient the tip properly, but also to wedge the catheter securely in the branch vessel. Other devices which simply modify the distal catheter curve may aid in tip orientation for vessel selection, but fail to provide the anchorage which is necessary to prevent catheter dislodgement.

In addition, prior designs could be improved in that the radii which the prior devices are able to make (to enter a vessel at a sharp angle, for example) have heretofore been severely limited.

In addition, the size of prior designs has made them less desirable for many applications.

SUMMARY OF THE INVENTION

Among the various objects and features of the present invention may be noted the provision of a catheter which simplifies the catheterization procedure.

A second object is the provision of such a catheter which significantly reduces the number of catheterizations required for any particular medical procedure.

A third object is the provision of such a catheter which can be easily and simply reshaped into a variety of different shapes as desired by the user.

A fourth object is the provision of such a catheter which can mimick almost any catheter configuration, and can thereafter be reformed in the body to other desired shapes.

A fifth object is the provision of such a catheter which obviates the need for multiple catheter exchanges, thereby reducing the time involved in a medical procedure and also reducing the possibility of complications.

A sixth object is the provision of such a catheter which provides adequate anchorage of the catheter against the aortic wall to reduce the "jet effect."

A seventh object is the provision of such a catheter which capable of achieving an improved curve radius at its distal end.

An eighth object is the provision of such a catheter which is significantly reduced in size compared to the prior devices.

Other objects will be in part apparent and in part pointed out hereinafter.

Briefly, a transformable catheter of the present invention includes a sheath having a diameter sufficiently small so that the sheath may be inserted into blood vessels of the human body. The sheath has a length which is a substantial fraction of the entire length of the transformable catheter, and has a bore therethrough running substantially from the proximal end of the sheath to the distal end of the sheath. A preformed inner catheter is part of the transformable catheter The inner catheter has a complex curve formed into the distal end thereof, and is sized to fit in the sheath bore and being axially movable with respect to the sheath in the bore. The sheath is sufficiently rigid and at least the tip of the inner catheter is sufficiently pliable so that withdrawal of the inner catheter into the sheath substantially irons out the complex curve of the distal tip so long as the distal tip remains substantially within the sheath. The distal tip resumes its complex curve shape upon movement thereof completely out of the sheath bore. The inner catheter has a length substantially corresponding to the length of the transformable catheter At least one wire runs from the proximal end of the sheath to the vicinity of the distal end of the sheath. The wire is connected to the sheath adjacent the distal end so as to allow the distal tip of the sheath to be deflected upon movement of the wire. By suitable manipulation of the wire and of the inner catheter with respect to the sheath, the shape of the exposed portion of the distal end of the inner catheter may be reformed or transformed, while in the human body, to any of a variety of shapes as desired by the user.

Although the invention is described in connection with blood vessels, it is not so limited. It may be used not only in arterial and venous branches, but also in the biliary tree, urinary tract, body cavities (such as the thorax and abdomen), hollow viscous organs (such as the stomach, intestines, and urinary bladder), cysts and abscesses—in short, in any place where selective direction and reformation of a catheter, tube or guidewire is required.

The method of the present invention includes changing the shape of a catheter in a human body. It includes the steps of inserting a combination catheter into a cavity of a human body. The combination catheter has a sheath with a length which is a substantial fraction of the entire length of the combination catheter. The combination catheter also has a preformed inner catheter with a complex curve formed into the distal end thereof disposed in the bore of the sheath. The user axially moves the inner catheter with respect to the bore to expose only so much of the distal end of the inner catheter as to cause the exposed portion of the distal end of the inner catheter to take a desired shape.

BRIEF DESCRIPTION OF THE DRAWINGS

Similar reference characters indicate similar parts throughout the several views of the drawings.

DESCRIPTION OF THE PREFERRED EMBODIMENT

Figure 1A:
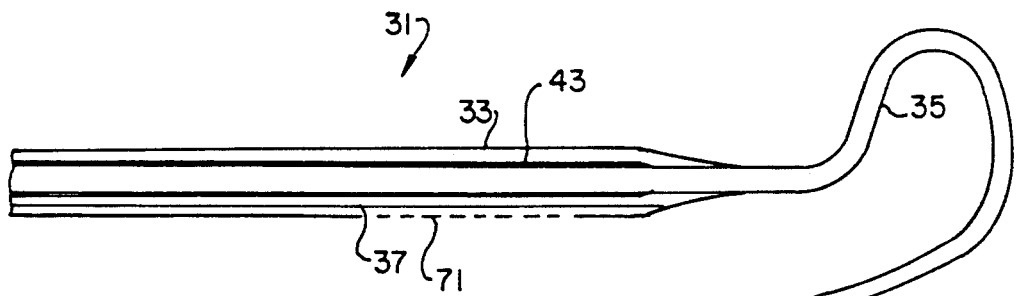
FIGS. 1A-1B, and 1D are side elevations illustrating the construction of the transformable catheter of the present invention.
Figure 1B:
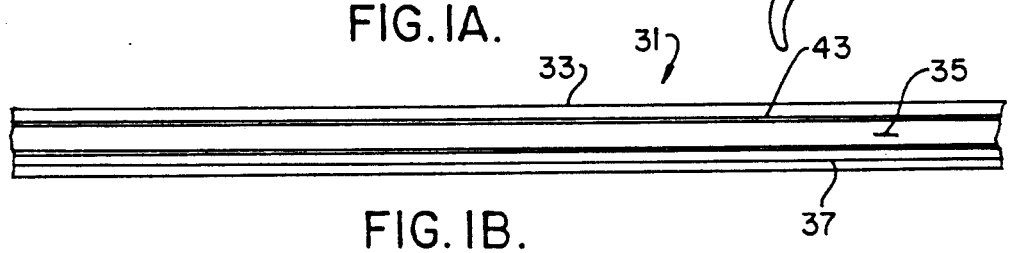
Figure 1C:
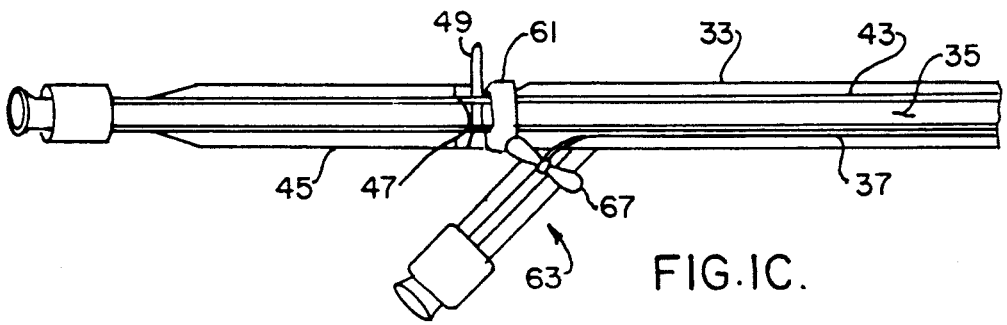
FIG. 1C is a top plan of the proximal portion of the transformable catheter of the present invention.

A catheter 31 (see FIGS. 1A-1C) of the present invention in its simplest form includes an enabling sheath 33, and an inner catheter 35 having a distal tip with a complex-curve shape. Catheter 31 is especially suited for selective arterial catheterization. In that application, the catheter is custom shaped or formed while in the patient to make it easy to direct the tip in any orientation required to enter a branching orifice or serpiginous vessel. Catheter 31 is not a steerable catheter, but rather one which may be custom curved and recurved by the user to select each branch vessel The catheter may also be used in the biliary tree and urinary tract to negotiate branches, corners, and serpiginous pathways.

As will become apparent in view of the following disclosure, manipulation of catheter 31 results in mimicking virtually any simple or complex curved configuration of selective arterial catheter shape imaginable while the catheter is disposed in the patient Likewise, modification of curve and tip orientations allow selection and direction of wire guides for other invasive procedures such as percutaneous cholangiography and percutaneous nephrostomy; that is, any procedure requiring direction or redirection of a catheter.

Inner catheter 35 is a complex memory curve catheter which runs in a coaxial manner through enabling sheath 33. With the complex tip completely extended beyond the sheath, the most complex tip configuration reforms. By pulling the inner catheter back through the enabling sheath to varying degrees (sheathing and unsheathing the inner catheter tip), various segments of the curve are "ironed out"—thereby changing the overall catheter tip configuration and tip orientation. The inner catheter is the active primary component but is a passive passenger with respect to the enabling sheath which acts upon the catheter to modify its shape. In addition, the fact that the transformation takes place in a vessel in the human body further modifies the shapes which can be achieved due to interaction of the transformable catheter with the walls of the vessel Sheath 33 has the capability of being formed by a pullwire 37 into a hook configuration, as described below. (Although described as a wire, item 37 could equivalently be made of high tensile strength suture or thread material.) This capability allows reformation of the complex memory curvature by directing the catheter tip downward while transformable catheter 31 is disposed in the aorta. Secondarily the sheath curve can, to some degree, act on the catheter to further modify the catheter shape.

In detail, transformable catheter 31 (see FIGS. 1A-1C) includes outer enabling sheath 33 which extends almost the entire length of the catheter. It is preferred that sheath 31 be long enough so that only the complex curve distal end portion of the inner catheter extend beyond it. Inner catheter 35 is disposed in the central bore of sheath 33 and has the most exaggerated sidewinder preformed tip configuration distally. (Of course, any other similar complex-shaped memory curve inner catheter could also be used in the present invention as inner catheter 35.)

The distal end of enabling sheath 33 can be formed into a curve with up to one hundred and eighty degrees of curvature when retracted by pull wire 37 by the suitable application of tension to the pull wire. This allows the hook configuration of the sheath 33 to reform the catheter 35 when the catheter is advanced through the sheath. The variable curved tip also allows variation in the degree of curvature, modifying the natural memory curve and thereby the overall shape of the catheter.

Figure 2A:
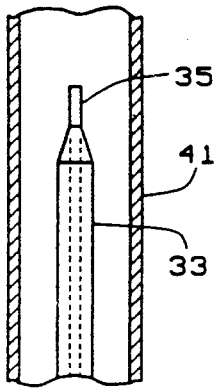
FIGS. 2A-2D are simplified elevations illustrating some of the myriad shapes which are attainable with the transformable catheter of the present invention.

Enabling sheath 33 modifies the extreme natural curvature of catheter 35 by acting as a housing that irons out various segments of the curvature when the catheter is retracted back into the sheath. Such an "ironing" effect is illustrated in FIG. 2A. In FIGS. 2 and 3, the various portions of transformable catheter 31 are shown in simplified form for clarity. For example, in FIG. 2A, the catheter 35 is shown extending distally from sheath 33 a small amount, while catheter and sheath are disposed in a vessel (such as an artery) 41.

Figure 2B:
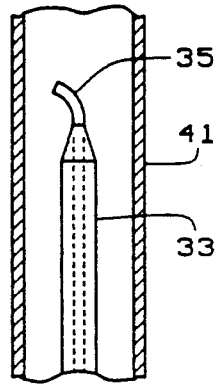
Figure 2C:
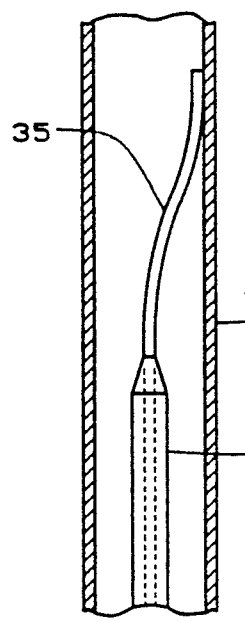

In FIG. 2B, the same catheter 35 is shown extended distally out of sheath 33 a small additional amount such that the catheter regains some of its curvature. Similarly, in FIGS. 2C and 2D, catheter 35 is extended distally even further. Note that in FIG. 2D, the distal curved portion of catheter 35 is fully extended from sheath 33, but the original configuration of catheter 35 is not obtained because of the interaction of the catheter with vessel wall 41.

Figure 3A:
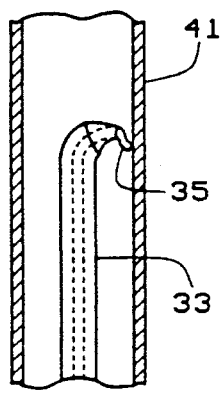
FIGS. 3A-3C are simplified elevations illustrating the reformation of a complex catheter shape inside the human body.
Figure 3B:
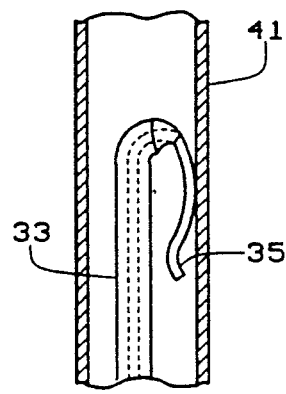
Figure 3C:
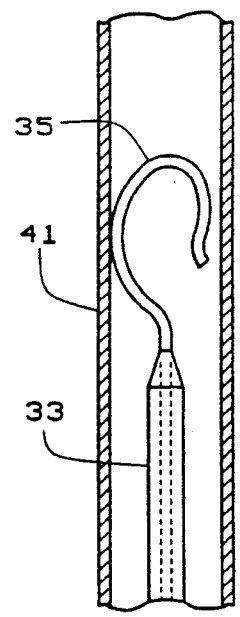

If the physician desires to instead shape or form catheter 35 back into its original, preformed shape of FIG. 1, the steps illustrated in FIGS. 3A-3C are followed. In this case, the sheath is first formed (by use of retraction wire 37) into the shape shown in FIG. 3A and FIG. 3B. As a result of this shape of the sheath, as catheter 35 is moved distally with respect to the sheath it assumes the form in the vessel as illustrated in FIGS. 3A and 3B. The sheath is restraigthened by suitable manipulation (i.e., release) of retraction wire 37 as shown in FIG. 3C as desired This procedure allows the original form of catheter 35 to be obtained in the vessel.

Figure 2D:
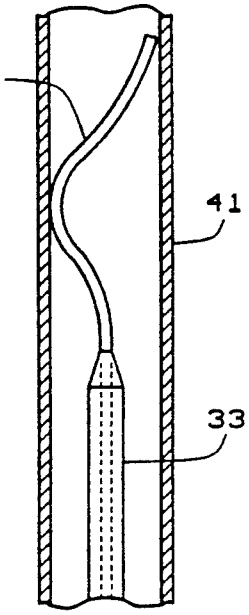

Note, from comparing FIG. 2D with FIG. 3C, the great differences in catheter shape achievable by simple manipulation of sheath 33 and of the catheter with respect to the sheath. In fact FIGS. 2A-2D and 3A-3C all illustrate some of the multitude of different catheter shapes which may be formed in the body, during a medical procedure, using the present invention. It should be realized that these shapes are merely illustrative and that with suitable manipulation of the sheath and relative movement between the sheath and the catheter, a great number of additional catheter configurations may be achieved.

Note as well, that the particular configuration shown in FIG. 3B provides a tighter radius for the tip of catheter 31 than is achievable with prior devices due to the interaction of complex-formed tip of the inner catheter and the deflection of the sheath. This greater flexibility in the shapes achievable permits vessels to be entered with the present catheter which were not readily accessible with the prior devices.

Referring back to FIGS. 1A-1C, the inner catheter 35 travels through the enabling sheath in a coaxial manner, but is stiffened from its proximal end to a point just proximal to the distal exaggerated curvatures by an outer stiffening segment 43. This outer stiffening segment is fused to the inner catheter proximally and distally and provides sufficient strength to the inner catheter to permit it to be moved axially with respect to the sheath without collapsing or binding.

Transformable catheter 31 is introduced in the usual manner through the femoral artery and advanced into the abdominal aorta. The catheter is reformed and selectively shaped in the abdominal aorta. When initially introduced the inner catheter is in its ironed parked position within the enabling sheath with only a small distal tip segment protruding (see FIG. 2A). The pull wire 37 is retracted, forming a hooked curve (see FIG. 3A) which allows direction of the catheter tip downward and thereby easy reformation of the memory curve. Once reformed, the various shapes of the catheter can be selected by advancing or retracting the catheter into the enabling sheath, thereby allowing or disallowing the natural memory curves to form at various segments. Pull wire modification of the enabling sheath allows additional curved configurations.

Figure 1D:
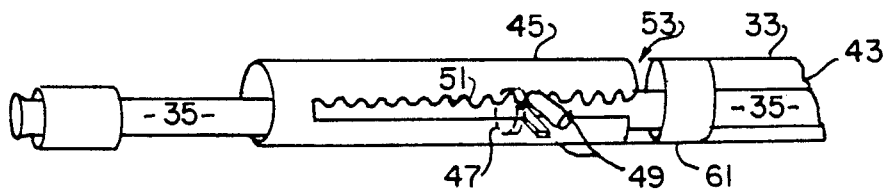
Figure 1E:
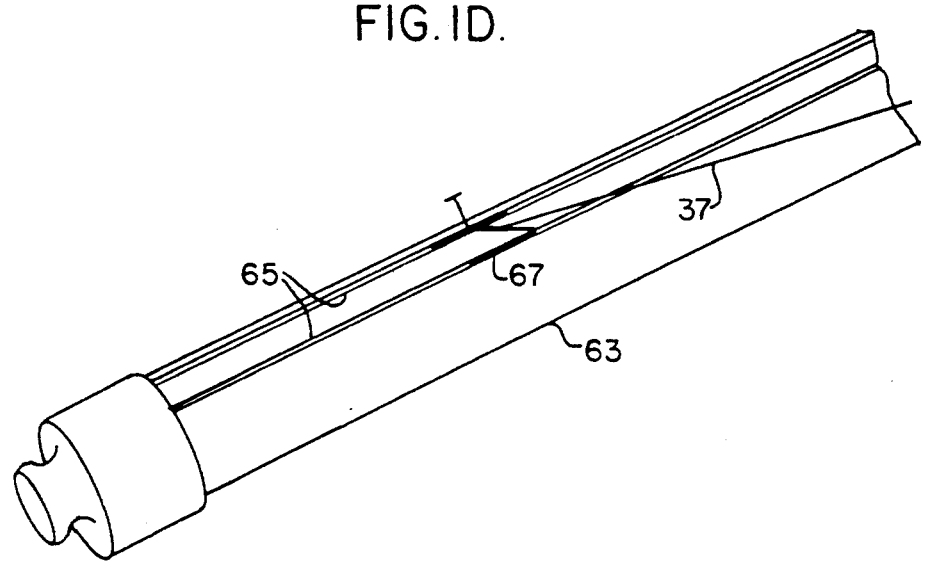
FIG. 1E is a view, similar to FIG. 1D but on an enlarged scale, illustrating the construction of a side port of the transformable catheter of the present invention.

Proximally, the stiffened inner catheter is pulled back through a plastic sleeve 45, slotted on either side. (See FIGS. 1C and 1D.) A fixation collar 47 attaches to the proximal portion of the catheter. A molded spring "V" prong 49, rounded on one side and flat on the other, arises from the side of the collar and extends through the sleeve. The prong is fixedly secured to catheter 35 and can be pulled through a right slot 51 of the sleeve (see FIG. 1D), thereby pulling the catheter as a whole through the enabling sheath and ironing out various degrees of memory curve in the distal tip of the catheter. The spring "V" prong 49 when squeezed together passes freely through the slot whose border is straight inferiorly but serrated superiorly as shown in FIG. 1D. When released the prong springs open and the rounded segment locks in a chosen serrated position. Distally, a crossing slot 53 allows the prong to be pulled across to the left slot (similar in size and shape to the right slot 51 shown), thereby twisting and torquing the entire catheter one hundred and eighty degrees so that when the prong 49 is pulled back in the left slot position the curved configuration is ironed out, resulting in additional variations in catheter shape. The locking pattern of the left slot is opposite to that of the right —flat upper border, serrated lower border, still allowing collar locking in various retracting positions.

The inner catheter proximally must exit through a valve (such as hemostasis valve 61 shown in FIG. 1C) as found in current arterial sheaths. A "Y" branch side port 63 allows constant pressure flushing of the sheath to prevent possible clot formation and allows water activation of the hydrophilic retraction wire.

On top of the side port 63, slide tracks 65 (see FIG. 1E) are molded. The tracks contain a plastic "S" spring slide 67 with locking teeth. The slide spring is attached to the pull wire 37 proximally. As the slide spring is disengaged by pushing downward and pulling back, the wire is retracted. When released the "S" slide locks into the selected position in the track. When straightening of the enabling sheath is desired, the slide 67 is disengaged and pushed to the forward position, thereby releasing traction on the wire and allowing the enabling sheath to reform spontaneously or with help by sliding the reinforced catheter towards the tip or by placing a straightening wire guide through the inner catheter lumen.

The ventral primary curvature segment of the enabling sheath is biased (as indicated at the reference numeral 71, FIG. 1A) to curve in a desired direction by making the sidewall along the inner portion of the desired curve more flexible due to the type or thickness of the material in this segment. Similarly, a flexibility bias can be established by designing exposed or covered gaps along one side of a segment of the sheath over which the bend is desired. When pulled distally, the more flexible or gapped side of the segment will give first, thereby, allowing curvature in a precisely selected segment and direction.

In view of the above, it will be seen that the various objects and features of the present invention are achieved and other advantageous results obtained. The examples of the present invention disclosed herein are intended to be illustrative, and

What is claimed is:

1. A transformable catheter comprising:
   a sheath having a straight relaxed shape and having a diameter sufficiently small so that the sheath may be inserted into the human body, said sheath having a length which is a substantial fraction of the entire length of the transformable catheter, and having a bore therethrough running substantially from the proximal end of the sheath to the distal end of the sheath;
   a preformed inner catheter having a complex curve formed into the distal end thereof, said preformed catheter being sized to fit in the sheath bore and being axially movable with respect to the sheath in the bore, said sheath being sufficiently rigid and the inner catheter being sufficiently pliable so that withdrawal of the inner catheter into the sheath substantially irons out the curve of that portion of the distal tip which is disposed in the sheath, said distal tip resuming its complex curve shape upon movement thereof completely out of the sheath bore, said inner catheter having a length substantially corresponding to the length of the transformable catheter, said complex curve having at least three curve portions having different radii of curvature, at least one of said curve portions having a direction of curvature retrograde to that of at least two of the other curve portions;
   at least one wire running from the proximal end of the sheath to the vicinity of the distal end of the sheath, said wire being connected to the sheath adjacent the distal end so as to allow the distal tip of the sheath to be deflected from the straight relaxed shape upon movement of said wire;

whereby by suitable manipulation of the wire and of the inner catheter with respect to the sheath the shape of the exposed portion of the distal end of the inner catheter may be reformed and transformed to any of a variety of shapes as desired by the user.

2. The transformable catheter as set forth in claim 1 wherein the sheath includes at its distal end a predetermined region of weakness so that upon tension being applied to the wire, the distal end of the sheath bends in the direction of the predetermined region of weakness.

3. The transformable catheter as set forth in claim 2 wherein upon removal of the tension from the wire, the sheath to return to its original straight relaxed shape.

4. The transformable catheter as set forth in claim 1 wherein the distal tip of the inner catheter is substantially more pliable than the body of the inner catheter, whereby the inner catheter has sufficient strength to support axial and rotational movement thereof with respect to the sheath.

5. The transformable catheter as set forth in claim 1 further including means for holding the inner catheter longitudinally in place with respect to the sheath at a plurality of positions.

6. The transformable catheter as set forth in claim 1 further including means for rotating the inner catheter with respect to the sheath to allow formation of different catheter shapes at different rotational positions of the inner catheter.

7. The transformable catheter as set forth in claim 1 wherein the sheath includes a lumen extending substantially from the proximal to the distal end thereof in which the wire is disposed.

8. The transformable catheter as set forth in claim 1 wherein there is only one wire running from the proximal end of the sheath to the vicinity of the distal end of the sheath.

9. A method of changing the shape of a catheter in a human body, comprising the steps of:

inserting a combination catheter into a cavity of a human body, said combination catheter having a sheath with a straight relaxed shape and with a length which is a substantial fraction of the entire length of the combination catheter, said combination catheter also having a preformed inner catheter with a complex curve formed into the distal end thereof disposed in the bore of the sheath, said preformed inner catheter extending distally from the distal end of the sheath during insertion into the human body and during use;

axially moving the inner catheter to a first longitudinal position with respect to the sheath to expose only so much of the distal end of the inner catheter as to cause the exposed portion of the distal end of the inner catheter to take a first desired shape, wherein the distal end of the inner catheter can take a plurality of shapes depending upon the amount of the distal end which is exposed;

mechanically holding the inner catheter against longitudinally movement in the first longitudinal position;

releasing the inner catheter and axially moving the inner catheter with respect to the sheath to a second longitudinal position to cause the exposed portion of the distal end of the inner catheter to take a second desired shape;

mechanically holding the inner catheter against longitudinal movement in the second longitudinal position; and deflecting the distal end of the sheath by selectively applying tension to a pull wire attached to said distal end to direct the distal end of the inner catheter in any of a plurality of desired directions and to modify at least one of the first and second shapes.

10. The method of changing the shape of a catheter in a human body as set forth in claim 9 wherein the shape of the distal end of the inner catheter is affected by contact with the wall of the cavity in which the catheter is disposed.

11. The method of changing the shape of a catheter in a human body as set forth in claim 9 wherein the deflecting step includes first deflecting the distal end of the sheath in a direction such that the preformed complex curve of the distal end of the inner catheter may be reformed inside the human body, and then further extending the distal end of the inner catheter distally out of the sheath to reform the complex curve of the distal end of the inner catheter inside the human body.

12. The method of changing the shape of a catheter in a human body as set forth in claim 9 wherein the distal end of the sheath is deflected and the distal tip of the inner catheter is exposed in an amount to cause the distal end of the combination catheter to assume a radius smaller than the radius achievable by deflecting the distal end of the sheath alone.

13. The method of changing the shape of a catheter in a human body as set forth in claim 9 wherein the distal end of the sheath is deflected by selectively applying tension to a wire disposed in the sheath.

14. A method of changing the shape of a catheter in a human body, comprising the steps of:

inserting a combination catheter into a cavity of a human body, said combination catheter having a sheath with a straight relaxed shape and with a length which is a substantial fraction of the entire length of the combination catheter, said combination catheter also having a preformed inner catheter with a complex curve formed into the distal end thereof disposed in the bore of the sheath, said preformed inner catheter extending distally from the distal end of the sheath during insertion into the human body and during use;

rotating the inner catheter with respect to the sheath to a first rotational position with respect to the sheath;

mechanically holding the inner catheter against rotational movement in the first rotational position;

releasing the inner catheter and rotationally moving the inner catheter with respect to the sheath to a second rotational position;

mechanically holding the inner catheter against rotational movement in the second rotational position; and deflecting the distal end of the sheath by selectively applying tension to a pull wire attached to said distal end to modify the shape of the combination catheter while the inner catheter is in at least one of the first and second rotational positions, whereby different catheter shapes are formed at different rotational positions of the inner catheter.

15. A method of changing the shape of a catheter in a human body, comprising the steps of:

inserting a combination catheter into a cavity of a human body, said combination catheter having a substantially straight sheath with a length which is a substantially fraction of the entire length of the combination catheter, said combination catheter also having a preformed inner catheter with a complex curve formed into the distal end thereof disposed in the bore of the sheath, said preformed inner catheter extending distally from the distal end of the sheath during insertion into the human body and during use;

axially moving the inner catheter with respect to the bore to expose only so much of the distal end of the inner catheter as to cause the exposed portion of the distal end of the inner catheter to take a desired shape, wherein the distal end of the inner catheter can take a plurality of shapes depending upon the amount of the distal end which is exposed;

mechanically fixing the inner catheter in place with respect to the sheath when a desired shape is achieved; and deflecting the distal end of the sheath by selectively applying tension to a pull wire attached to said distal end to modify the achieved shape.

16. The method of changing the shape of a catheter in a human body as set forth in claim 15 wherein the combination catheter is formed into a plurality of distinct shapes in the human body during a single medical procedure further including mechanically fixing the inner catheter in place with respect to the sheath for each of the plurality of distinct shapes.

17. A transformable catheter comprising:

a substantially straight sheath having a diameter sufficiently small so that the sheath may be inserted into the human body, said sheath having a length which is substantial fraction of the entire length of the transformable catheter, and having a bore therethrough running substantially form the proximal end of the sheath to the distal end of the sheath;

a preformed inner catheter having a complex curve formed into the distal end thereof, said preformed catheter being sized to fit in the sheath bore and being axially movable with respect to the sheath in the bore, said sheath being sufficiently rigid and the inner catheter being sufficiently pliable so that withdrawal of the inner catheter into the sheath substantially irons out the curve of that portion of the distal tip which is disposed in the sheath, said distal tip resuming its complex curve shape upon movement thereof completely out of the sheath bore, said inner catheter having a length substantially corresponding to the length of the transformable catheter, said complex curve having at least three curve portions having different radii of curvature, at least one of said curve portions having a direction of curvature, at least one of said curve portions having a direction of curvature retrograde to that of at least two of the other curve portions;

at least one wire running from the proximal end of the sheath to the vicinity of the distal end of the sheath, said wire being connected to the sheath adjacent the distal end so as to allow the distal tip of the sheath to be deflected upon movement of said wire;

whereby by suitable manipulation of the wire and of the inner catheter with respect to the sheath the shape of the exposed portion of the distal end of the inner catheter may be reformed and transformed to any of a variety of shapes as desired by the user;

means for holding the inner catheter longitudinally in place with respect to the sheath at a plurality of positions;

wherein the means for holding the inner catheter longitudinally in place with respect to the sheath at a plurality of positions includes means for mechanically locking the inner catheter in place with respect to the sheath, said means for mechanically locking being manually operable to unlock the inner catheter with respect to the sheath for longitudinally movement with respect thereto.

18. The transformable catheter as set forth in claim 17 wherein the means for mechanically locking includes a slot and pin locking mechanism.

19. A transformable catheter comprising:

a substantially straight sheath having a diameter sufficiently small so that the sheath may be inserted into the human body, said sheath having a length which is a substantial fraction of the entire length of the transformable catheter, and having a bore therethrough running substantially from the proximal end of the sheath to the distal end of the sheath;

a preformed inner catheter having a complex curve formed into the distal end thereof, said preformed catheter being sized to fit in the sheath bore and being axially movable with respect to the sheath in the bore, said sheath being sufficiently rigid and the inner catheter being sufficiently pliable so that withdrawal of the inner catheter into the sheath substantially irons out the curve of that portion of the distal tip which is disposed in the sheath, said distal tip resuming its complex curve shape upon movement thereof completely out of the sheath bore, said inner catheter having a length substantially corresponding to the length of the transformable catheter, said complex curve having at least three curve portions having different radii of curvature, at least one of said curve portions having a direction of curvature retrograde to that of at least two of the other curve portions;

at least one wire running from the proximal end of the sheath to the vicinity of the distal end of the sheath, said wire being connected to the sheath adjacent the distal end so as to allow the distal tip of the sheath to be deflected upon movement of said wire;

whereby by suitable manipulation of the wire and of the inner catheter with respect to the sheath the shape of the exposed portion of the distal end of the inner catheter may be reformed and transformed to any of a variety of shapes as desired by the user;

further including mechanical means for locking the inner catheter in at least two different rotational positions with respect to the sheath, said mechanical means for locking being manually operable for unlocking the inner catheter with respect to the sheath for movement to another rotational position with respect thereto.

20. A method of changing the shape of a catheter in a human body, comprising the steps of:

inserting a combination catheter into a cavity of a human body, said combination catheter having a substantially straight sheath with a length which is a substantial fraction of the entire length of the combination catheter, said combination catheter also having a preformed inner catheter with a complex curve formed into the distal end thereof disposed in the bore of the sheath, said preformed inner catheter extending distally from the distal end of the sheath during insertion into the human body and during use;

axially moving the inner catheter with respect to the bore to expose only so much of the distal end of the inner catheter as to cause the exposed portion of the distal end of the inner catheter to take a desired shape, wherein the distal end of the inner catheter can take a plurality of shapes depending upon the amount of the distal end which is exposed;

deflecting the distal end of the sheath by selectively applying tension to a pull wire attached to said distal end to direct the distal end of the inner catheter in any of a plurality of desired directions and to attain a plurality of shapes;

said combination catheter being formed into a plurality of distinct shapes in the human body during a single medical procedure, said forming step including forming the combination catheter into the plurality of distinct shapes in the human body during a single medical procedure to catheterize all the vessels necessary for a cerebral arteriogram.

21. A method of changing the shape of a catheter in a human body, comprising the steps of:

inserting a combination catheter into a cavity of a human body, said combination catheter having a substantially straight sheath with a length which is a substantial fraction of the entire length of the combination catheter, said combination catheter also having a preformed inner catheter with a complex curve formed into the distal end thereof disposed in the bore of the sheath, said preformed inner catheter extending distally from the distal end of the sheath during insertion into the human body and during use;

axially moving the inner catheter with respect to the bore to expose only so much of the distal end of the inner catheter as to cause the exposed portion of the distal end of the inner catheter to take a desired shape, wherein the distal end of the inner catheter can take a plurality of shapes depending upon the amount of the distal end which is exposed;

deflecting the distal end of the sheath by selectively applying tension to a pull wire attached to said distal end to direct the distal end of the inner catheter in any of a plurality of desired directions and to attain a plurality of shapes;

said combination catheter being formed into a plurality of distinct shapes in the human body during a single medical procedure, said forming step including forming the combination catheter into the plurality of distinct shapes in the human body during a single medical procedure to catheterize all the vessels necessary for a visceral arteriogram.

22. A method of changing the shape of a catheter in a human body, comprising the steps of:

inserting a combination catheter into a cavity of a human body, said combination catheter having a substantially straight sheath with a length which is a substantial fraction of the entire length of the combination catheter, said combination catheter also having a preformed inner catheter with a complex curve formed into the distal end thereof disposed in the bore of the sheath, said preformed inner catheter extending distally from the distal end of the sheath during insertion into the human body and during use;

axially moving the inner catheter with respect to the bore to expose only so much of the distal end of the inner catheter as to cause the exposed portion of the distal end of the inner catheter to take a desired shape, wherein the distal end of the inner catheter can take a plurality of shapes depending upon the amount of the distal end which is exposed;

deflecting the distal end of the sheath by selectively applying tension to a pull wire attached to said distal end to direct the distal end of the inner catheter in any of a plurality of desired directions and to attain a plurality of shapes;

said combination catheter being formed into a plurality of distinct shapes in the human body during a single medical procedure, said forming step including during a single medical procedure forming the combination catheter into a shape having a first distal configuration, catheterizing a first vessel while the combination catheter is in the first shape, forming the combination catheter into a second shape having a second distal configuration without removing the inner catheter from the sheath, and catheterizing a second vessel while the combination catheter is in the second shape, said first distal configuration having at least one less radii of curvature than the second distal configuration, the distal tip of the combination catheter in the first distal configuration pointing substantially opposite the direction of the distal tip of the combination catheter in the second distal configuration.

23. A method of changing the shape of a catheter in a human body, comprising the steps of:

inserting a combination catheter into a cavity of a human body, said combination catheter having a substantially straight sheath with a length which is a substantial fraction of the entire length of the combination catheter, said combination catheter also having a preformed inner catheter with a complex curve formed into the distal end thereof disposed in the bore of the sheath, said preformed inner catheter extending distally from the distal end of the sheath during insertion into the human body and during use;

axially moving the inner catheter with respect to the bore to expose only so much of the distal end of the inner catheter as to cause the exposed portion of the distal end of the inner catheter to take a desired shape, wherein the distal end of the inner catheter can take a plurality of shapes depending upon the amount of the distal end which is exposed; and deflecting the distal end of the sheath by selectively applying tension to a pull wire attached to said distal end to direct the distal end of the inner catheter in any of a plurality of desired directions and to attain a plurality of shapes;

wherein the deflecting step includes first deflecting the distal end of the sheath in a direction such that the preformed complex curve of the distal end of the inner catheter may be reformed inside the human body, and then further extending the distal end of the inner catheter distally out of the sheath to reform the complex curve of the distal end of the inner catheter inside the human body;

wherein the reformation of the preformed complex curve occurs in the abdominal aorta.

* * * * *

UNITED STATES PATENT AND TRADEMARK OFFICE
CERTIFICATE OF CORRECTION

PATENT NO. : 5,290,229
DATED : March 1, 1994
INVENTOR(S) : Larry D. Paskar,

It is certified that error appears in the above-identified patent and that said Letters Patent is hereby corrected as shown below:

Column 6, line 36, after "and" add--are not to be construed in a limiting

--sense.--;
Column 7, line 16, after "sheath" add --attempts--;

Column 7, line 62, delete "longitudinally" and insert --longitudinal--;
Column 9, line 2, delete "substantially" and insert --substantial--.

Signed and Sealed this

Twentieth Day of September, 1994

Attest:

BRUCE LEHMAN

*Attesting Officer*  *Commissioner of Patents and Trademarks*